US00PP25603P3

(12) United States Plant Patent
Hammond

(10) Patent No.: US PP25,603 P3
(45) Date of Patent: May 26, 2015

(54) ***GAURA* PLANT NAMED 'GBAPI01-0'**

(50) Latin Name: *Gaura lindheimeri*
Varietal Denomination: GBAPI01-0

(71) Applicant: Frank Hammond, Narre Warren East (AU)

(72) Inventor: Frank Hammond, Narre Warren East (AU)

( * ) Notice: Subject to any disclaimer, the term of this patent is extended or adjusted under 35 U.S.C. 154(b) by 146 days.

(21) Appl. No.: 13/815,548

(22) Filed: Mar. 7, 2013

(65) Prior Publication Data

US 2014/0259247 P1 Sep. 11, 2014

(51) Int. Cl.
*A01H 5/02* (2006.01)

(52) U.S. Cl.
CPC ..... *A01H 5/02* (2013.01)
USPC ..... Plt./432

(58) Field of Classification Search
USPC ..... Plt./432
See application file for complete search history.

(56) References Cited

U.S. PATENT DOCUMENTS

PP13,189 P2 * 11/2002 Bentley ..... Plt./226

* cited by examiner

*Primary Examiner* — Anne Grunberg
(74) *Attorney, Agent, or Firm* — Cassandra Bright

(57) ABSTRACT

A new and distinct *Gaura lindheimeri* cultivar named 'GBAPI01-0' is disclosed, characterized by exceptionally short plants of very compact habit, stems and foliage flushed with anthocyanin coloration as well as short peduncles and dark pink flowers. The new variety is a *Gaura*, and is normally used as an ornamental garden or container plant.

1 Drawing Sheet

Latin name of the genus and species: *Gaura lindheimeri*.
Variety denomination: 'GBAPI01-0'.

BACKGROUND OF THE INVENTION

The new cultivar is a product of chance discovery. The variety was discovered as a seedling of unknown parentage at a research nursery by the inventor, Frank Hammond, a citizen of Australia. The new variety was discovered by the inventor November of 2006.

Asexual reproduction of the new cultivar 'GBAPI01-0' was first performed by vegetative cutting in Victoria, Australia in July of 2007. 'GBAPI01-0' has since produced more than 5 generations by vegetative cuttings and has shown that the unique features of this cultivar are stable and reproduced true to type.

SUMMARY OF THE INVENTION

The cultivar 'GBAPI01-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GBAPI01-0'. These characteristics in combination distinguish 'GBAPI01-0' as a new and distinct *Gaura lindheimeri* cultivar:

1. Exceptionally short plants.
2. Very compact habit.
3. Stems and foliage flushed with anthocyanin coloration.
4. Short peduncles.
5. Dark pink flowers.

PARENT COMPARISON

Parent varieties are unknown.

COMMERCIAL COMPARISON

Plants of the new cultivar 'GBAPI01-0' are similar to plants of the commercial variety, *Gaura lindheimeri* 'Crimson Butterfly' U.S. Plant Pat. No. 13,189, in most horticultural characteristics. However, plants of the new cultivar 'GBAPI01-0' produces a darker pink colored flower than the comparator. In addition to a different flower color, the new cultivar 'GBAPI01-0' is shorter in height than the comparator.

BRIEF DESCRIPTION OF THE PHOTOGRAPH

The accompanying photograph in FIG. 1 illustrates in full color a typical plant of 'GBAPI01-0' grown in a greenhouse. The pot size is a commercial 6 inch pot. The plant shown is approximately 12 weeks old.

DETAILED BOTANICAL DESCRIPTION

In the following description, color references are made to The Royal Horticultural Society Colour Chart except where general terms of ordinary dictionary significance are used. The following observations and measurements describe 'GBAPI01-0' plants grown in a commercial controlled greenhouse in Oxnard, Calif. Temperatures ranged from 15° C. to 28° C. during the day and 18° C. to 22° C. at night. No artificial light, photoperiodic treatments or chemical treatments were given to the plants. Measurements and numerical values represent averages of typical plant types.
Botanical classification: *Gaura lindheimeri* 'GBAPI01-0'.

PROPAGATION

Time to initiate roots: 15 to 20 days at approximately 20° C.
Root description: Fibrous, colored near RHS Greyed-Orange 165D.

PLANT

Growth habit: Very compact, upright perennial.
Pot size of plant described: 6 inch.
Height: 25 cm.
Plant spread: 45 cm.
Growth rate: Rapid.
Branching characteristics: Basal branching, or nearly at soil level. Lateral branches produced approximately 2.0 cm above pinch to main stem. Upper lateral branches not produced.
Length of primary branches: Approximately 17 cm.
Diameter of branches: Approximately 0.35 cm.
Quantity of primary branches: Average 30.
Characteristics of primary lateral branches:
*Form*.—Irregular round, some flat sides.
*Color*.—Near RHS Red-Purple 59A.
*Texture*.—Scant pubescence.
*Strength*.—Strong, somewhat flexible.
Internode length: Average 1.8 cm.

FOLIAGE

Leaf:
*Arrangement*.—Alternate, simple.
*Quantity*.—Approximately 8 fully developed per branch and 12 immature leaves.
*Average length*.—4.5 cm.
*Average width*.—1.1 cm.
*Shape of blade*.—Elliptic.
*Apex*.—Acute.
*Base*.—Attenuate.
*Margin*.—Entire.
*Texture of top surface*.—Scant pubescence visible under magnification.
*Texture of bottom surface*.—Glabrous.
*Aspect*.—Undulating.
*Color*.—Young foliage upper side: Near RHS Greyed-Purple 187A. Young foliage under side: Near RHS Greyed-Purple 187B. Mature foliage upper side: Near RHS Green 137A. Mature foliage under side: Near RHS Green 137B.
*Venation*.—Type: Pinnate. Venation color upper side: Near RHS Green 137C, flushed near base Red-Purple 59B. Venation color under side: Near RHS Yellow-Green 145B.
*Petiole*.—Sessile.

FLOWER

Natural flowering season: Spring through Summer.
Inflorescence and flower type and habit: Single zygomorphic flowers produced on terminal and axillary racemes.
Persistent or self-cleaning: Self Cleaning.
Bud:
*Shape*.—Cylindric.
*Length*.—1.5 cm.
*Diameter*.—0.3 cm.
*Color*.—Near RHS Red-Purple 58A.
Raceme:
*Diameter*.—Average 4 cm.
*Length*.—Average 10 cm.
*Flowers per raceme*.—5 to 7.
Flower size:
*Diameter*.—Average 3.5 cm.
*Length*.—Average 2.5 cm.
Corolla/petals:
*Quantity of petals*.—4.
*Arrangement*.—Symmetrical whorl.
*Petal length*.—1.9 cm.
*Petal width*.—1.0 cm.
*Corolla tube length*.—1.8 cm.
*Corolla tube diameter*.—0.2 cm.
*Texture*.—Glabrous.
*Petal apex*.—Acute.
*Petal base*.—Attenuate.
*Petal shape*.—Spatulate.
*Margin*.—Entire.
*Aspect*.—Upwardly cupped.
*Petal color*.—When opening: Upper surface: Near RHS Red-Purple N66A. Lower surface: Near RHS Red-Purple N66A. Fully opened: Upper surface: Near RHS Red-Purple N57C. Lower surface: Near RHS Red-Purple N57C. Fading: Upper surface: Near RHS Red-Purple N57C. Lower surface: Near RHS Red-Purple N57C.
*Outer corolla tube color*.—Near RHS Red-Purple 58A.
*Inner corolla tube color*.—Near RHS Green 137A with heavy flush Red-Purple 58A.
Calyx/sepals:
*Quantity per flower*.—4.
*Shape*.—Linear.
*Length*.—1.7 cm.
*Width*.—0.3 cm.
*Apex*.—Acute.
*Base*.—Truncate.
*Margin*.—Entire.
*Texture*.—Glabrous.
*Aspect*.—Undulating and strongly reflexed back.
*Color:*.—Upper Surface: Near RHS Red-Purple 59C. Lower Surface: Near RHS Red-Purple 61A.
Peduncle:
*Length*.—Average 7.5 cm.
*Diameter*.—Approximately 0.2 cm.
*Color*.—Near RHS Green 137A flushed with Red-Purple 58A.
*Orientation*.—Straight, approximately 15 degree angle from stem.
*Texture*.—Glabrous.
*Strength*.—Strong.
Pedicel: Not present, directly attached by corolla tube to peduncle.
Fragrance: Very faint.

REPRODUCTIVE ORGANS

Stamens:
*Number*.—8.
*Filament length*.—Approximately 1.3 cm.
Anthers:
*Shape*.—Linear.
*Length*.—Approximately 0.3 cm.
*Color*.—Near RHS Greyed-Purple 187A.
*Pollen*.—Color: Near RHS Orange-White 159A. Quantity: Scant.
Pistil:
*Number*.—1.
*Length*.—2.5 cm.
*Style*.—Length: 2.5 cm. Color: Near RHS Red-Purple 73C with upper portion Red-Purple 67A.
*Stigma*.—Shape: Bi lobed. Color: Near RHS Yellow-White 158B.

*Ovary*.—Ovary Color: Near RHS Greyed-Purple 187B. Ovary Length: Approximately 1 cm. Ovary diameter: Approximately 0.1 cm. Ovary shape: Linear.

OTHER CHARACTERISTICS

Seeds and fruits: Not observed to date.

Disease/pest resistance: Neither resistance nor susceptibility to diseases or pests has been observed in this variety.

Temperature tolerance: The new variety tolerates temperatures from approximately −5° to 38° C.

What is claimed is:

1. A new and distinct cultivar of *Gaura* plant named 'GBAPI01-0' as herein illustrated and described.

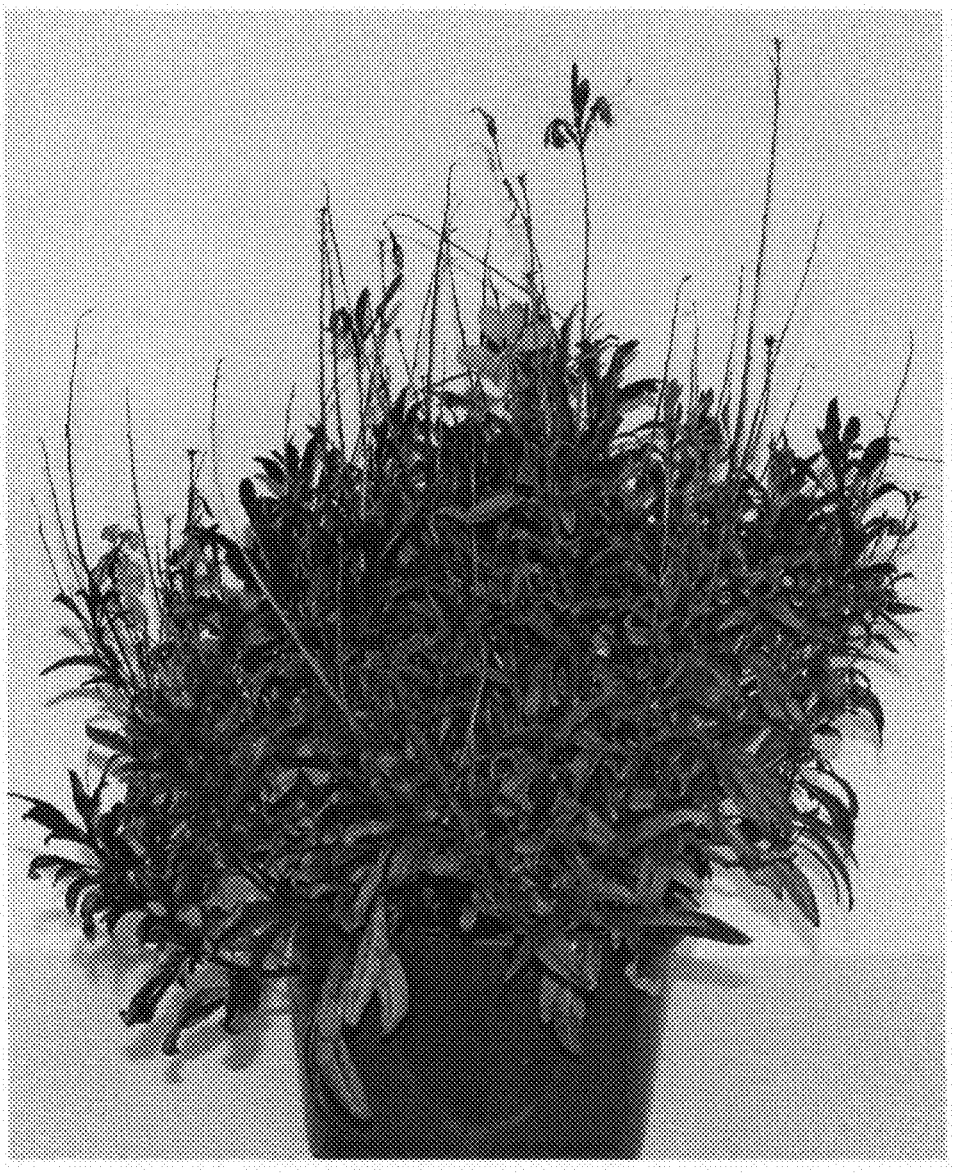

* * * * *